Jan. 8, 1957
Plant Pat. 1,549
M. N. WINKLER
CARNATION PLANT
Filed Feb. 8, 1956
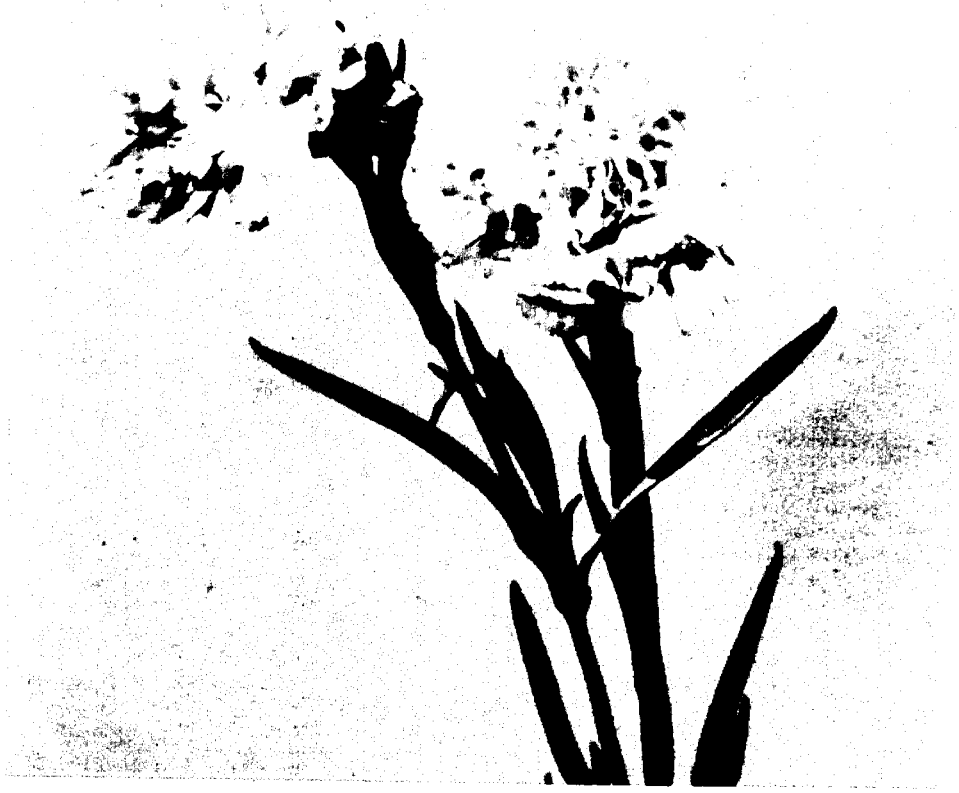
Inventor:
Marshall N. Winkler:
Robert L. Dennison
Attorney.

United States Patent Office

Plant Pat. 1,549

Patented Jan. 8, 1957

1,549

CARNATION PLANT

Marshall Norman Winkler, Wakefield, Mass.

Application February 8, 1956, Serial No. 564,334

1 Claim. (Cl. 47—60)

My invention relates to improvements in varieties of carnations, having for its principal object to produce a carnation of good commercial size and rapid growth, with a flower of attractive form and desirable color throughout the year, without bleaching during change of seasons.

A further object is to produce a carnation flower that keeps well and ships well even during the hot weather; that does not develop the upward curl of the petals that the usual light pink carnation develops in hot weather; that retains its turgid form and fresh appearance throughout the summer.

This carnation has been named the Edward Winkler.

*Parentage.*—The new variety was originated from a seedling hybridized from an unnamed seedling on Princess Irene, a carnation originated in Holland (not patented, to my knowledge) and asexually reproduced with distinguishing characteristics unchanged in several succeeding generations by means of cuttings, in county of Middlesex, State of Massachusetts.

The accompanying drawing shows in full color a specimen of my new carnation plant showing the flower.

The color shown in drawing does not quite reproduce the exact shade as described under color. For an accurate color refer to color chart hereinbelow mentioned.

The following is a detailed description of the plant and flower of my new carnation variety.

THE PLANT

*Growth habits.*—Fast growth and very productive. If not crowded when growing, each stem may have two or three cuttings or side shoots produced low enough so that the flower can be cut with a marketable length of stem and still leave a cutting to form a return crop. The general effect of a well grown plant of this variety is bushy, rather than lank and tall.

*Stems.*—Strong and stiff, attaining medium length; approximate 30″ (inches). Easy to support when growing, and holding its head high in cut flower arrangements.

*Leaves.*—The leaves are long, average 4″ to 5″ with medium width, average ⅜″, and stand away from the stem with a gradual curl. The side buds are small in comparison with the terminal bud. The leaves are grey green and are covered with a grey bloom that can be rubbed off by running the fingers over the surface.

THE FLOWER

*Form.*—Very full high center, flower viewed from the side when fully open forms a half sphere; slightly flattened.

*Size.*—The flower is large, averaging between 3½ inches to 4½ inches in diameter when open. It retains more of its size in hot weather than does the standard carnation.

*Fragrance.*—Strong for a colored carnation and differs from the usual carnation by having a refreshing peppermint odor rather than clove.

*Petals.*—A flower of this variety picked at random had one hundred petals on June 27th and on January 10th 80 petals. This count will vary somewhat with the season but the petal count will be high all season. The petals rise straight out of the calyx cup for a short interval before bending out to form the flower. This gives the effect of a tiny neck above the calyx. The usual carnation has petals that bend immediately over the calyx. The petals have very fine serrations along the edges and are long, averaging 2″ length from the calyx.

*Calyx.*—The cup of the calyx is slender for the size of the flower it contains averaging ⅝″ diameter measured at middle of cup. It comes up to five or six sepals that are bulbous—more so in the flowers that have five sepals than those with six. The sepals overlap somewhat with small earlike lobes where they intersect. The bulb that forms on the sepal strengthens the calyx as this flower almost never splits its calyx.

*Keeping qualities.*—The flower keeps and ships well, even during hot weather. It does not develop the upward curl in the petals that the usual light pink carnation has in hot weather. Instead it retains its turgid form and fresh appearance throughout the summer.

*Color.*—"Neyron Rose"—Tint #623.

From 623/2 in the center of the flower to 623/3 on the edge according to the Horticultural color chart published by the Royal Horticultural Society of England.

The carnation that most nearly resembles my seedling is "Light Pink Littlefield" (not patented).

My carnation differs from Light Pink Littlefield in the following respects:

The calyx on mine is smaller and more slender than that of Light Pink Littlefield (averages ¼″ less in diameter than Light Pink Littlefield).

The outer petals are almost ½″ longer than Light Pink Littlefield and they do not curl or bruise as easily on the edge as does Light Pink Littlefield.

The plant grows faster and comes into flower quicker by almost a month's time than does Light Pink Littlefield.

My new carnation produces one or two cuttings on most stems while Light Pink Littlefield is almost completely free from side cuttings. This trait of my flower in addition to its fast growth makes it a much more productive plant and therefore a more profitable variety to grow than is Light Pink Littlefield.

My variety also retains its shape and clear color without fading into the hot weather better than does Light Pink Littlefield.

The color of my carnation is more intense in the center and paler on the edge than is the color of Light Pink Littlefield.

The plants of my carnation grow about six inches taller than does Light Pink Littlefield.

Having thus disclosed my invention, I claim:

The new and distinct variety of carnation plant, substantially as herein shown and described, characterized particularly by its stiff stem of medium length; large size of flower of high centered, slightly flattened half spherical shape as viewed from the side; slight neck-like effect of petals as they emerge from the calyx; slender calyx, flaring out with bulbous shaped sepals; long petals of Neyron Rose color, more intense at the center and paler on the edge of the flower; and distinct peppermint fragrance.

No references cited.